United States Patent [19]

Bovy et al.

[11] Patent Number: 4,853,401
[45] Date of Patent: Aug. 1, 1989

[54] SPIRO-HYDANTOINS AS ALDOSE REDUCTASE INHIBITORS

[75] Inventors: Philippe R. Bovy, St. Louis, Mo.; Claude Gillet, Blanmont, Belgium; Albert Lenaers, Triel-sur-Seine, France; Paul Niebes, Grez-Doiceau, Belgium; Joseph Roba, Dion Valmont, Belgium; Georges Lambelin, Brussels, Belgium

[73] Assignee: G. D. Searle & Co., Chicago, Ill.

[21] Appl. No.: 33,427

[22] Filed: Apr. 1, 1987

[51] Int. Cl.⁴ .................. A61K 31/415; C07D 233/72
[52] U.S. Cl. ........................................ 514/389; 548/312
[58] Field of Search ................ 548/312, 308; 514/389

[56] References Cited

U.S. PATENT DOCUMENTS 4,117,230 9/1978 Sarges ................................. 548/309
4,438,272 3/1984 York ................................... 548/308

OTHER PUBLICATIONS

H. G. Hers, *Biochim., Biophys. Acta* 37, 120–6 (1960).

*Primary Examiner*—Richard A. Schwartz
*Attorney, Agent, or Firm*—J. Timothy Keane; Paul D. Matukaitis

[57] ABSTRACT

The invention relates to spirohydantoins of the formula I

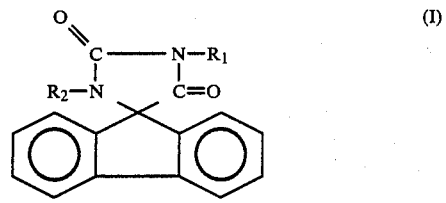

where $R_1$ and $R_2$ are defined hereinbelow. Also disclosed are methods of preparation, pharmaceutical compositions containing at least one of these compounds, and methods of using said compounds for treatment and prevention of complications of diabetes and galactosemia.

18 Claims, No Drawings

SPIRO-HYDANTOINS AS ALDOSE REDUCTASE INHIBITORS

BACKGROUND OF THE INVENTION

Aldose reductase (AR) is an enzymatic oxidoreduction system (Alditol-NADF oxidoreductase EC 1.1.1.21) which was first described in 1960/H. G. Hers, Biochim, Biophys. Acta 37, 120–6 (1960)/. The protein, with nicotinamide adenine dinucleotide phosphate (NADPH) as co-factor, catalyses the reduction of various aldoses or similar substances (aldehydes). In a well-balanced biological system it participates in a minor metabolic pathway of glucose, which it converts into sorbitol ("sorbitol pathway"). In diabetic hyperglycemia or galactosemia, the availability of an excess of aldose results in increased activity of the "sorbitol pathway". The result is an accumulation of sorbitol or galactitol in various tissues. This accumulation, which results in degeneration of the tissues where it occurs, has been located inter alia at the crystalline lens (diabetic cataract), nerves (neuropathy), endothelial cells (vasculopathy), kidneys (nephropathy), retina (retinopathy) and the $\beta$ cells of the pancrease (aggravation of diabetes). This degeneration in diabetics can be prevented by blocking this metabolic pathway of glucose.

Diabetes is a common disease which strikes about 4% of the population. It is a chronic, crippling disease. The degenerative complications of this disease are at present the main problem facing diabetes specialists.

The reason is that treatment with hypoglycemiating agents cannot keep glycemia constant at a normal value and consequently cannot completely prevent accumulation of sorbitol in the cells. Any treatment for preventing or correcting these degenerative anomalies will of course have a wide range of application.

Compounds containing a hydantoin nucleus have already been described as inhibitors of aldose reductase.

Belgian PS No. 859 824, for example, describes a series of "spiro-hydantoins", the most active of which is d-6-fluoro-spiro-/chromane-4,4'-imidazolidine/-2',5'-dione (sorbinil).

Other spiro-hydantoins such as spiro-/fluorene-9,4'-imidazolidine/-2',5'-dione are also described in EPA No. 0 092 358.

The applicants have discovered a new class of spiro-fluorene-hydantoin derivatives having a powerful inhibiting effect of aldose reductase "in vivo". These novel compounds are characterised by the presence of well-defined substituents fixed to one or two nitrogen atoms of the hydantoin nucleus, and by the absence of substituents on the fluorenyl group.

It is well known in the literature that, in general, hydantoin-type compounds have numerous disadvantages such as non-negligible toxicity, a teratogenic effect, serious side effects and difficult absorption.

The applicants have discovered that substitution of the hydantoin nucleus of spiro-/fluorene-9,4'-imidazolidine/-2',5'-dione by suitably chosen radicals can yield products free from toxicity or undesirable side-effects. This substitution also yields products having improved physico-chemical characteristics and biological activity compared with the corresponding non-substituted products.

Compared with spiro-fluorene-hydantoins substituted on the fluorenyl group, the products according to the invention are very easy to prepare, by simple non-laborious methods from raw materials which are commercially available or easy to synthesize.

The derivatives according to the invention correspond to the general formula I:

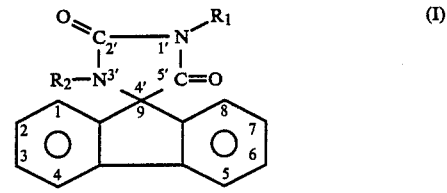

in which:

$R_1$ and $R_2$, which may or may not be identical, represent:

(a) Hydrogen or (b) A CH—OR$_4$ group in which R$_3$ represents:

(1) Hydrogen (2) A straight-chain or branched $C_1$, $C_2$, $C_3$ or $C_4$ alkyl group or (3) A phenyl group, R$_4$ represents:

(1) Hydrogen (2) A straight-chain or branched $C_1$, $C_2$, $C_3$, $C_4$, $C_5$, $C_6$, $C_7$, $C_8$, $C_9$ or $C_{10}$ alkyl group, (3) A $C_3$, $C_4$, $C_5$, $C_6$, $C_7$ or $C_8$ cycloalkyl group (4) A straight-chain or branched $C_1$, $C_2$, $C_3$ or $C_4$ alkyl group substituted by:

(a) A phenyl or phenoxy group, or (b) a phenyl or phenoxy group substituted by one or more $C_1$, $C_2$, $C_3$ or $C_4$ alkyl or $C_1$, $C_2$, $C_3$ or $C_4$ alkoxy radicals are by one or two atoms of fluorine, chlorine or bromine (5) A phenyl group, substituted if required by one or two $C_1$, $C_2$, $C_3$, $C_4$ alkyl or $C_1$, $C_2$, $C_3$, $C_4$ alkoxy radicals or by one or two atoms of fluorine, chlorine or bromine (6) A

group in which

R$_5$ represents:

(a) A straight-chain or branched $C_1$, $C_2$, $C_3$, $C_4$, $C_5$, $C_6$, $C_7$, $C_8$, $C_9$ or $C_{10}$ alkyl group (b) A $C_5$, $C_6$ or $C_7$ cycloalkyl group (c) A straight-chain or branched $C_1$, $C_2$, $C_3$, $C_4$ or $C_5$ alkyl group substituted by a radical chosen from among the following group:

A $C_5$, $C_6$, $C_7$ cycloalkyl radical,

A phenyl or phenoxy radical,

A phenyl or phenoxy radical substituted by one, two or three straight-chain or branched $C_1$, $C_2$, $C_3$, $C_4$ alkyl or $C_1$, $C_2$, $C_3$, $C_4$ alkoxy groups or by one or two atoms of fluorine, chlorine or bromine, (d) A phenyl group or (e) An —NH—R$_6$ group in which R$_6$ represents hydrogen or a straight-chain or branched $C_1$, $C_2$, $C_3$, $C_4$ alkyl group or a phenyl group (f) An —O—R$_7$ group in which R$_7$ represents a straight-chain or branched $C_1$, $C_2$, $C_3$, $C_4$ alkyl group or a phenyl or benzyl group, the groups R$_1$ and R$_2$ may not simultaneously be hydrogen, and stereoisomers and mixtures thereof and salts of these compounds formed with pharmaceutically useful metals or organic bases.

A preferred embodiment of the invention relates to formula I compounds in which $R_1$ and $R_2$ represent a group $CHR_3$—$OR_4$ in which $R_3$ represents hydrogen or a $C_1$–$C_4$ alkyl group and $R_4$ represents a group —CO—$R_5$ in which $R_5$ represents a straight-chain or branched $C_1$–$C_{10}$ alkyl group or a straight-chain or branched $C_5$–$C_7$ cycloalkyl group or a straight-chain or branched $C_1$–$C_5$ alkyl radical substituted by a $C_5$–$C_7$ cycloalkyl group.

In a preferred class of formula I products, $R_1$ and/or $R_2$ represents hydrogen or a group $CHR_3$—O—CO—$R_5$ in which $R_3$ represents hydrogen or a methyl group and $R_5$ represents a straight-chain or branched $C_1$–$C_{10}$ alkyl group with the restriction that $R_1$ and $R_2$ do not simultaneously represent hydrogen.

In another preferred class of formula I products, $R_1$ and $R_2$ represent the group —$CHR_3$—$OR_4$ in which $R_3$ represents hydrogen or a $C_1$–$C_4$ alkyl group and $R_4$ represents the group CO—O—$R_7$ in which $R_7$ can be a $C_1$–$C_4$ alkyl group or a phenyl group or a benzyl group.

Another preferred form of the invention relates to formula I derivatives in which $R_1$ and/or $R_2$ represents hydrogen or the group $CHR_3$—$OR_4$ in which $R_3$ represents hydrogen or a $C_1$–$C_3$ alkyl group and $R_4$ represents hydrogen or a straight-chain or branched $C_1$–$C_5$ alkyl group, with the restriction that $R_1$ and $R_2$ do not simultaneously represent hydrogen.

In a very important class of formula I products, $R_1$ and/or $R_2$ represent hydrogen or a group $CHR_3$—O—$R_4$ in which $R_4$ represents a phenyl group substituted if required by one or two methyl or methoxy radicals or by one or two atoms of fluorine, chlorine or bromine, with the restriction that $R_1$ and $R_2$ do not simultaneously represent hydrogen.

A particularly important class of products is that in which the compounds correspond to formula I in which $R_1$ and/or $R_2$ represent hydrogen or a $CHR_3$—$OR_4$ group in which $R_3$ represents hydrogen or a $C_1$–$C_4$ alkyl group and $R_4$ has one of the following values: a straight-chain or branched $C_1$–$C_{10}$ alkyl or $C_3$–$C_8$ cycloalkyl or $C_1$–$C_4$ alkyl group substituted by a phenyl or phenoxy group also substituted if required, with the restriction that $R_1$ and $R_2$ are not simultaneously hydrogen.

Another preferred class of formula I products is that in which $R_1$ and $R_2$ represent the group $CHR_3$—$OR_4$ in which $R_3$ represents hydrogen or a $C_1$–$C_4$ alkyl group and $R_4$ corresponds to the CO—NH—$R_6$ group in which $R_6$ represents hydrogen or a $C_1$–$C_4$ alkyl or phenyl.

Another preferred form of the invention relates to formula I compounds in which $R_1$ and $R_2$ represent a $CHR_3$—$OR_4$ group in which $R_3$ represents hydrogen or a $C_1$–$C_4$ alkyl group and $R_4$ represents the group CO—$R_5$ in which $R_5$ represents a phenyl group or a $C_1$–$C_5$ alkyl group substituted by a phenyl or phenoxy group which are also substituted if required.

A final preferred form of the invention relates to formula I compounds in which $R_1$ and/or $R_2$ represent hydrogen or a group $CHR_3$—$OR_4$ in which $R_3$ represents a phenyl group, with the restriction that $R_1$ and $R_2$ are not simultaneously hydrogen.

The products according to the invention comprising one or more centres of asymmetry can be used either in the form of mixtures containing a number of diastereoisomers in any relative proportions, or in the form of the pure diastereoisomers.

Also, pairs of enantiomers may be present in equal (racemic) or unequal proportions.

Finally, the product may be used in the form of the optically pure compound.

The invention also covers pharmaceutical compositions in which the active ingredient is at least one compound having the general formula I or a salt thereof, with an excipient used in galenic pharmacy.

The compositions are prepared suitable for oral, rectal, parenteral or local administration.

They can be solids or liquids or gels and, depending on the method of administration, can be presented in the form of powders, tablets, dragées, coated tablets, capsules, granulates, syrups, suspensions, emulsions, solutions, suppositories or gels.

The compositions may also contain another therapeutic agent having a simiolar or different activity from the products according to the invention.

The products according to the invention can be used for treatment and prevention of complications of diabetes and galactosemia, e.g. neuropathy, cataracts, retinopathy, nephropathy or vasculopathy.

The following are examples of compounds according to the invention:

bis-(1′,3′-hydroxymethyl)-spiro-[fluoroene-9,4′-imidazolidine]-2′,5′-dione bis-(1′,3′-acetoxymethyl)-spiro-[fluorene-9,4′-imidazolidine]-2′,5′-dione bis-(1′,3′-n.octanoyloxymethyl-spiro-[fluorene-9,4′-imidazolidine]-2′,5′-dione bis-(1′,3′-ethoxycarbonyloxymethyl)-spiro-[fluorene-9,4′-imidazolidine]-2′,5′-dione 1′-methoxymethyl-spiro-[fluorene-9,4′-imidazolidine]-2′,5′-dione 1′-acetoxymethyl-spiro-[fluorene-9,4′-imidazolidine]-2′,5′-dione bis-(1′,3′-N-phenylcarbamyloxymethyl)-spiro-[fluorene-9,4′-imidazolidine]-2′,5′-dione bis-[1′,3′-(4-cyclohexylbutanoyloxymethyl)]-spiro-[fluorene-9,4′-imidazolidine]-2′,5′-dione 1′-[1-(2,2-dimethylpropanoyloxy)ethyl]-spiro-[fluorene-9,4′-imidazolidine]-2′,5′-dione.

bis-(1′,3′-propanoyloxymethyl)-spiro-[fluorene-9,4′-imidazolidine]-2′,5′-dione.

The compounds according to the invention can be obtained by a method which also forms part of the invention and consists in substituting one or both hydrogen atoms of the hydantoin group of spiro-/fluorene-9,4′-imidazolidine/-2′,5′-dione, product II, which can be performed in one or more steps by known methods.

The process is illustrated by diagram 1 hereinafter.

In this and the following diagrams, the spiro-/fluorene-9,4′-imidazolidine/-2′,5′-dione group will be represented as follows:

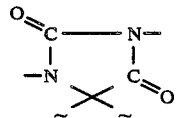

In diagram 1, $R_3$ and $R_4$ have the previously-defined values, A represents the group $OR_4$ or a group which can be converted into group $OR_4$, e.g. a hydroxyl or $C_1$–$C_4$ alkoxy group, and B represents an atom or radical easily substituted by the group $CR_4$, e.g. an atom of chlorine, bromine or iodine or an alkylsulphonate or arylsulphonate group such as O-methyl or O-tosyl.

ate reaction conditions and more particularly controlling the stoichiometric ratio of the reagents (Diagram 2a).

Diagram 1

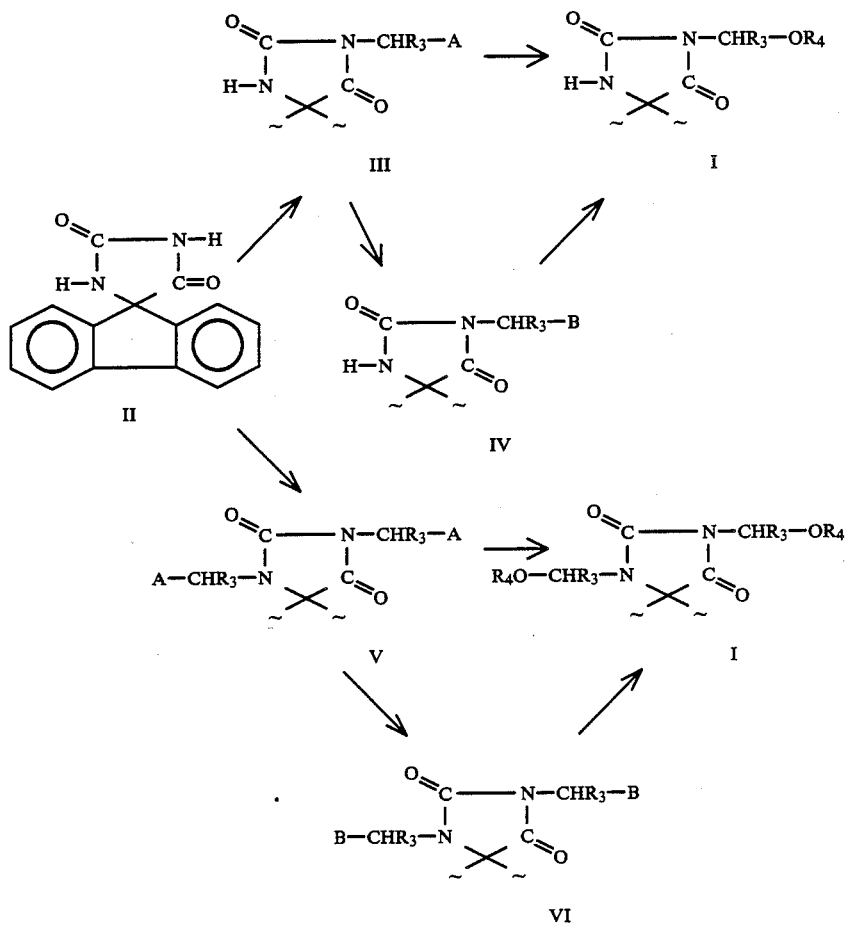

In a first method, formula I compounds can be obtained by substituting compound II by hydroxyalkylation, followed if required by acylation or alkylation. This method is perfectly suitable for preparing monosubstituted formula I derivatives, by choosing appropriate reaction conditions and more particularly controlling the stoichiometric ratio of the reagents (Diagram 2a).

However, this method is particularly important for preparing disubstituted formula I derivatives, since dihydroxyalkylation is easily performed and usually with very high yields (Diagram 2b).

Diagram 2a

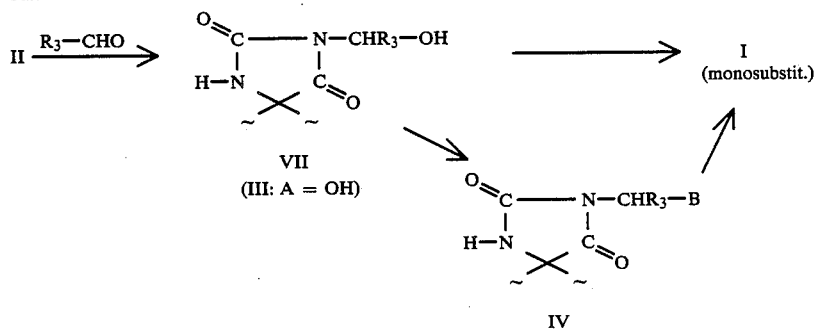

Diagram 2b

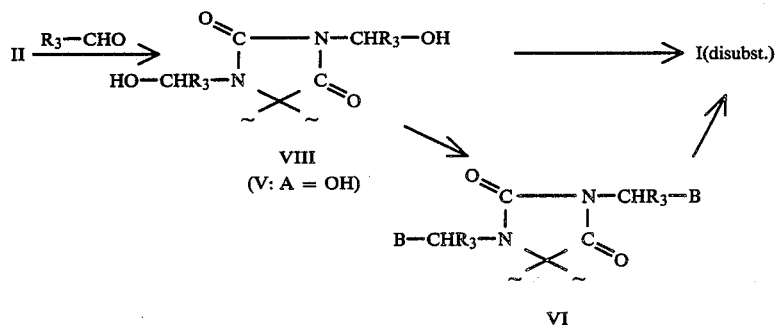

In diagrams 2a and 2b, groups $R_3$ and B have the previously-defined values and group OH corresponds to one of the values of A in compound III or V in diagram 1.

1.1 The hydantoin nucleus is hydroxyalkylated in conventional manner by reacting spiro-/fluorene-9,4'-imidazolidine/-2',5'-dione (II) with an aldehyde having the formula $R_3$—CHO.

In general, compound II is dissolved or suspended in a solvent such as water, if required in the presence of a co-solvent, e.g. an alcohol such as methanol.

The reagent $R_3$—CHO is used either as such or dissolved in a suitable solvent. Alternatively, it ca be used in a protected form, e.g. an acetyl having the formula $R_3$—CH(OR$_{13}$)$_2$ in which $R_2$ represents a $C_1$-$C_3$ alkyl group, or in the form of a polymer such as paraformaldehyde.

The temperature of the reaction medium is normally chosen between $-15°$ C. and ambient temperature. In the case where $R_3$ is different from hydrogen, it may be advantageous to carry out the reaction at a higher temperature, even up to the reflux temperature of the reaction medium. The presence of a base or acid will catalyse the reaction.

In order to form disubstituted formula VIII derivatives, hydroxyalkylation is generally carried out using an excess of the aldehyde $R_3$—CHO.

On the other hand, when preparing monosubstituted formula VII derivatives, a strictly metered quantity of aldehyde $R_3$—CHO is reacted with compound II, usually by continuous addition of small quantities of aldehyde.

The reaction product is isolated by conventional methods such as filtration, decantation or extraction and can be converted into a formula I compound or a formula IV or VI intermediate with or without preliminary purification.

1.2 Formula VII or VIII intermediate products can be converted into a formula I compound, in which $R_4$ represents the group CO—$R_5$, by acylation by conventional methods illustrated in Diagrams 3a and 3b hereinafter.

Diagram 3a

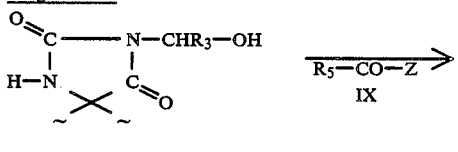

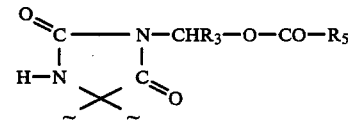

In diagrams 3a and 3b, $R_3$ and $R_5$ have the previously specified values and Z is such that the group CO—Z can represent a carboxyolic or alkoxy carbonyl group (—CCOR$_8$, in which $R_8$ represents a $C_1$-$C_4$ alkyl radical or a benzyl or alkyl or phenyl radical substituted so as to activate ester IX for the purpose of nucleophilic substitution), an acid halide group (CO—X) in which X represents an atom of fluorine, chlorine, bromine or iodine or an anhydride group (—CO—O—CO—$R_9$, $R_9$ being an $R_5$ group or a $C_1$-$C_4$ alkyl, phenyl or benzyl radical) or an N-carbonylimidazolyl $$(-CO-N\underset{\diagdown\!=\!\diagup}{\overset{\diagup\!=\!\diagdown}{\phantom{N}}}N)$$

group.

The acylation reagent $R_5$—CO—Z(IX) may also represent a cetene having the formula $$\underset{R_{11}}{\overset{R_{10}}{\diagdown}}C=C=O$$

in which $R_{10}$ and $R_{11}$ are such that the group

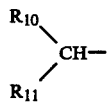

corresponds to one of the alkyl, cycloalkyl or substituted alkyl groups represented by $R_5$.

The acylation group $R_5-CO-Z$ (IX) may also represent a chloroformate having the formula $R_7O-CO-Cl$ (X) in which $R_7$ has the previously-defined values.

If, in the reagent $R_5-CO-Z$ (IX), the group $CO-Z$ is e.g. an acid halide, anhydride or an N-carbonylimidazolyl group or if $R_5-CO-Z$ represents a cetene or chloroformate, acylation is usually performed by reacting reagent IX with alcohol VII or VIII either in an inert solvent or using one of the reagents as solvent. If the reagent is an acid halide or anhydride or chloroformate, the reaction is preferably performed in the presence of at least one equivalent of a base which can be organic, e.g. triethylamine or pyridine, or inorganic e.g. a carbonate or bicarbonate of an alkali or alkaline earth metal.

Depending on the reactivity of the acylation agent, a stoichiometric or excess quantity is used, and the reaction occurs at a temperature which may vary from below room temperature to the reflux temperature of the reaction medium.

When in reagent $R_5-CO-Z$ (IX) the $CO-Z$ group is carboxylic or alkoxycarbonyl ($-COOR_8$), esterification or transesterification can be carried out in numerous ways.

Conventionally, acid IX or ester IX are reacted with alcohol VII or VIII under anhydrous conditions and in the presence of an acid catalyst such as sulphuric acid or para-toluene sulphonic acid or a strongly acid ion-exchange resin. The solvent can be either one of the reagents or an inert solvent. The reaction is advantageously performed with an excess of one of the reagents, the reaction medium being heated.

Another method consists in continuously eliminating the water or alcohol $R_8-OH$ formed during the reaction, e.g. by distillation or azeotropic distillation using an appropriate solvent. The reaction conditions are similar to those described hereinbefore except that one reagent need not be used in a large excess.

A third method consists in reacting alcohol VII or VIII in an inert solvent and under anhydrous conditions with a stiochiometric quantity of carboxylic acid IX in the presence of a coupling agent such as 1,1'-carbonyldiimidazole or dicyclohexylcarbodiimide.

1.3 Conversion of the intermediate product of formula VII or VIII into a fomula I compound in which $R_4$ represents a $C_1-C_{10}$ alkyl or a $C_3-C_8$ cycloalkyl or a $C_1-C_4$ alkyl group substituted by a phenyl or phenoxy group substituted if required as previously mentioned, is performed by alkylation by known methods, illustrated hereinafter in diagrams 4a and 4b.

Diagram 4a

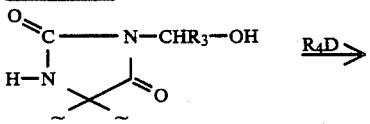

VII

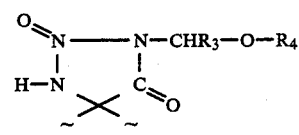

I

Diagram 4b

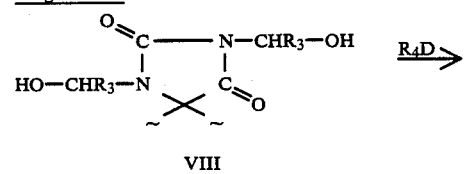

VIII

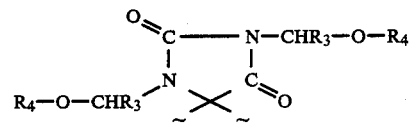

I $R_4$ has the previously-mentioned values, $R_3$ represents the previously specified groups and D represents an easily substitutable group, e.g. an atom of chlorine, bromine or iodine or an alkyl or aryl sulphonate or a sulphate easily substituted by alcohol VII or VIII. Alkylation is conventionally brought about by reacting the reagents in a solvent such as acetone or an aliphatic or aromatic hydrocarbon or dimethylformamide or hexamethylphosphortriamide, preferably in the presence of an organic base such as a tertiary amine or pyridine or an inorganic base such as a carbonate or bicarbonate or alkali or alkaline earth metal hydroxide.

The reaction is definitely brought about at the reflux temperature of the reaction medium.

1.4 Conversion of a formula VII or VIII intermediate product into a formula I compound in which $R_4$ represents a phenyl group substituted if required, is conventionally brought about by converting alcohol VII or VIII into a formula IV or VI intermediate (see diagram 2) which is subsequently converted into a formula I compound by reaction with a phenol or phenolate having the formula $R_4OH$ or $R_4O^-$ in which $R_4$ represents a phenyl group substituted if required as previously defined.

The conversion of alcohol VII or VIII is described hereinafter in Sections 1.5 and 1.6.

1.5 In a variant of the acylation and alkylation processes described in Sections 1.2 to 1.4, the intermediate formula VII or VIII alcohols can be converted into a formula I derivative via an intermediate formula IV or VI product (see diagrams 2a and 2b).

1.5.1 Intermediates IV or VI in which B represents a halogen atom such as chlorine, bromine or iodine are obtained by well-known methods e.g. by treating alcohol VII or VIII with a halogenation agent such as a halogenated hydracid, e.g. hydrochloric or hydrobromic acid or an inorganic acid halide such as phosphorus tribromide or phosphorus pentachloride or phosphorus trichloride or thionyl chloride or by reaction with a halogen such as bromine or iodine in the presence of red phosphorus (diagrams 5a and 5b).

Diagram 5a

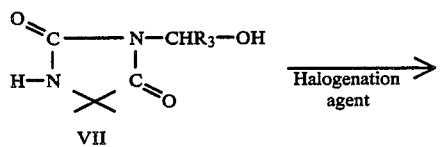

Diagram 5b

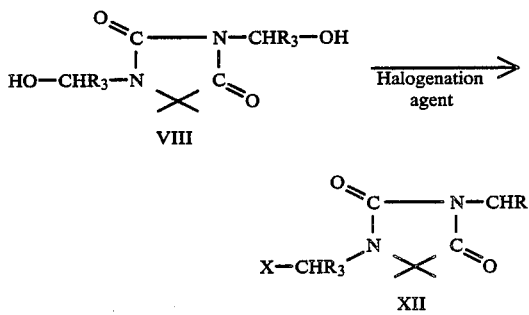

X represents an atom of chlorine, bromine or iodine. The reaction with a halogenated hydracid is advantageously performed by reflux-heating the reaction medium, if required in an inert solvent such as an aliphatic or aromatic or chlorinated hydrocarbon, the water formed during the reaction being preferably eliminated e.g. by azeotropic distillation with a suitable solvent.

The reaction with an inorganic acid halide or a halogen in the presence of red phosphorus is performed in an inert solvent at a temperature which is usually between ambient temperature and the reflux temperature of the reaction medium and advantageously in the presence of an agent for capturing the halogenated hydracid formed, e.g. an organic or inorganic base such as pyridine, triethylamine or an alkali metal carbonate.

Halogenated compounds XI and XII are isolated by conventional methods such as filtration, distillation or extraction.

The reactions and reaction conditions for this conversion will be chosen so as not to affect the other groups in the molecule.

1.5.2 When group B in the formula IV or VI intermediates represents a sulphonate group, the products are easily obtainable by reacting a formula VII or VIII alcohol with a sulphonyl chloride having the formula $R_{12}$—$SO_2Cl$ ($R_{12}$ representing a $C_1$-$C_4$ alkyl or an aryl group such as p-tolyl) (diagrams 6a and 6b).

Diagram 6a

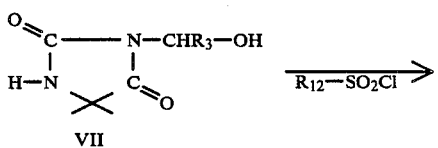

-continued

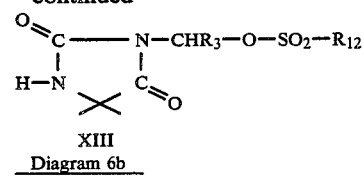

Diagram 6b

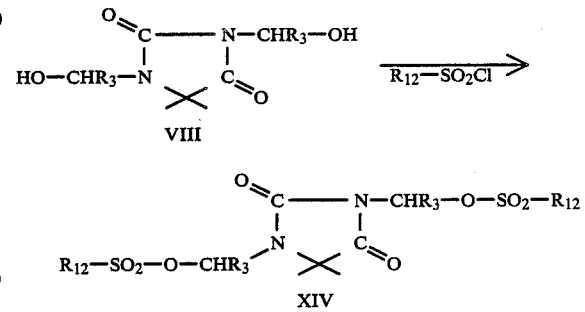

The reaction is preferably performed in the presence of an organic base such as pyridine or triethylamine, or an inorganic base such as a carbonate or bicarbonate of an alkali or alkaline earth metal.

The solvent can be an organic base such as pyridine or an inert solvent such as an ether or aliphatic or aromatic hydrocarbon, which may or may not be chlorinated.

The reaction is normally brought about at ambient temperature or by moderately heating the reaction medium.

One of the main advantages of this method is the ease of purifying formula XIII or XIV sulphonates by crystallization.

1.6 Conversion of intermediate IV or VI in which B represents a halogen or a sulphonate group into a formula I compound is brought about in conventional manner by reacting the intermediate with a carboxylic acid having the formula $R_5$—COOH, $R_5$ having the previously-defined values, or with its metal salt or salt of addition with a nitrogenated organic or inorganic base such as an ammonium trialkylammonium salt or, depending on the nature of the $R_4$ group, by reacting the intermediate with a phenol or phenolate having the formula $R_4OH$ or $R_4O^-$, $R_4$ denoting a phenyl or substituted phenyl group as previously defined.

The reaction is brought about at a temperature between ambient temperature and the reflux temperature in a solvent such as acetone, water, a lower alcohol or pyridine, advantageously in the presence of an organic or inorganic base.

The reagents are normally used in stoichiometric quantities.

1.7 In a variant of the acylation process, in the case where, in the general formula I, $R_5$ represents a radical —NH—$R_6$ in which $R_6$ has the previously-mentioned values, compounds VII and VIII can be converted into a formula I derivative by condensation with an isocyanate having the formula $R_6$—N=C=O (XV), as per diagrams 7a or 7b.

Diagram 7a

-continued

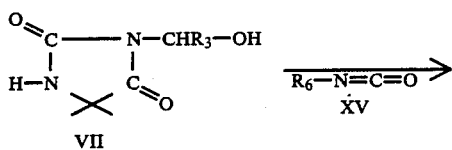
VII

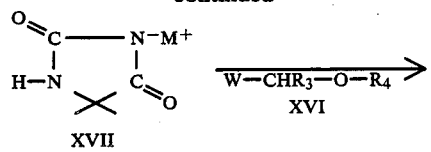
XVII

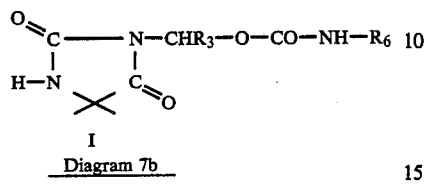
I
Diagram 7b

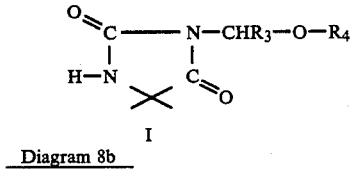
I
Diagram 8b

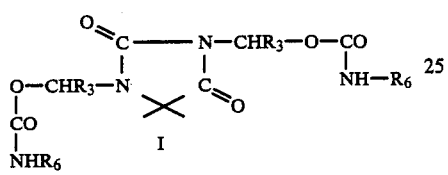
VIII

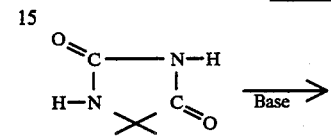
II

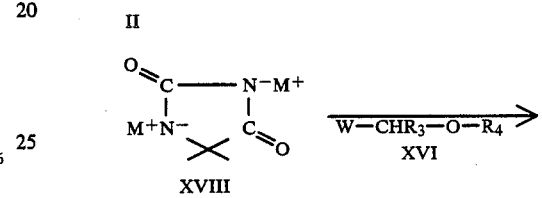
XVIII

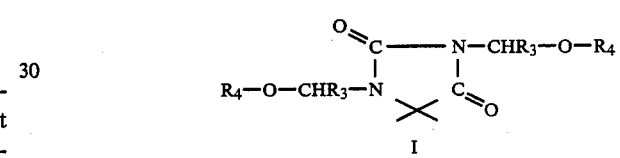
I

The reaction is brought about under anhydrous conditions by placing the reagents in an aprotic solvent having low polarity, e.g. an aliphatic or aromatic hydrocarbon or an ether or a polar solvent such as dimethylformamide or hexamethyl phosphortriamide.

When it is intended to prepare a mono-substituted compound I, a strictly metered quantity of isocyanate will be used.

To control the reaction more easily, the reagent is gradually added to the substrate, the reaction medium being cooled. At the end of the reaction it may be advantageous to heat the reaction mixture, if required to reflux, in order to complete the reaction.

2. In another method, formula I compounds can be obtained by substituting compound II or its alkali-metal salt by alkylation by an alkyl halide or sulphonate having the formula XVI (W—CHR$_3$—O—R$_4$) in which R$_3$ and R$_4$ have the previously-defined values except that R$_4$ does not denote hydrogen, and W represents an atom or group which is easily substitutable, e.g. chlorine, bromine, iodine or a sulphonate having the formula R$_{12}$—SO$_2$—O, R$_{12}$ having the previously-specified values (see Section 1.5.2.).

This method is illustrated by diagrams 8a and 8b, in which M$^+$ represents an alkali-metal cation.

Diagram 8a

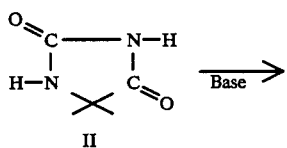
II

The reaction is brought about by reacting an alkali-metal salt having the formula XVII or XVIII under anhydrous conditions with an alkylation agent having the formula XVI. It is performed in an aprotic polar solvent such as dimethylformamide or hexamethylphosphortriamide. Advantageously the reaction medium is heated for several hours, if required to reflux, in an inert anhydrous atmosphere to complete the reaction.

The amount of reagent XVI will depend on the nature of the salt (mono-salt formula XVII or di-salt formula XVIII), and it will advantageously be used in slight excess over the stoichiometric quantity.

The formula I reaction product is isolated by conventional methods, e.g. treatment of the reaction medium with water followed by filtration of compound I if solid or by extraction. The formula XVII and XVIII alkali metal salts are prepared in conventional manner by treatment of compound II under anhydrous conditions with a strong base in a suitable solvent, e.g. sodium or potassium hydroxide in a lower alcohol, a sodium or potassium alcoholate in an alcohol, or sodium hydride in an aliphatic hydrocarbon. The stoichiometry of the reagents used and their nature will determine the type of salt formed (mono-salt XVII or di-salt XVIII).

Although of use in preparing di-substituted formula I compounds, this method is particularly useful for synthesizing mono-substituted formula I compounds, since a formula XVII mono-salt is formed more easily than a formula XVIII di-salt.

2.1 In a variant, formula I compounds in which R$_1$ and/or R$_2$ represent a —CHR$_3$—O—CO—R$_5$ group can be obtained by alkylation of compound II via salts XVII or XVIII, with an alpha-haloalkylether XIX; the formula XX or XXI intermediate ether formed is then converted to a formula I compound by a known method, e.g. by reaction with an anhydride having the formula $(R_5CO)_2O$ in which $R_5$ represents an alkyl or cycloalkyl or substituted alkyl or phenyl group as previously defined, in the presence of a Lewis acid catalyst such as tin tetrachloride.

This variant is illustrated in diagrams 9a and 9b hereinafter, in which $R_5$ has the values defined hereinbefore and $M^+$ represents an alkali-metal cation.

Diagram 9a

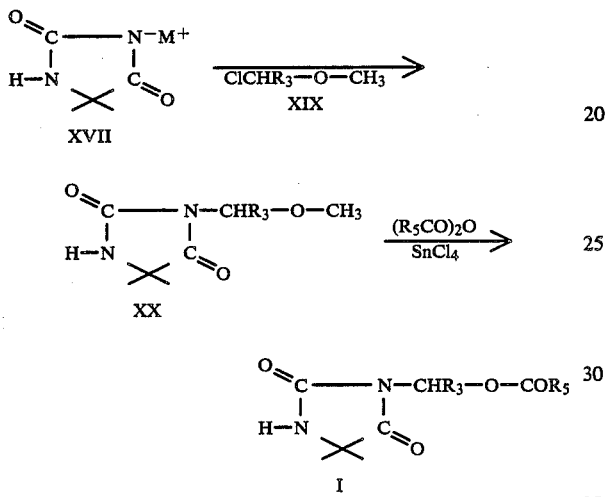

Diagram 9b

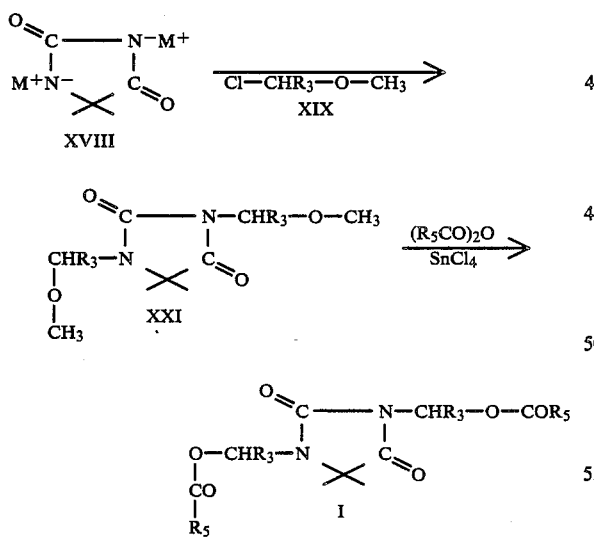

Salts XVII or XVIII are alkylated under the same conditions as described for reagent XVI hereinbefore (see diagram 8a) and the intermediate formula XX or XXI ether is converted by agitating a solution or suspension of ether XX or XXI at ambient temperature under anhydrous conditions for several hours in an excess of anhydride $(R_5CO)_2O$ in the presence of the catalyst.

2.2 A variant of this method consists in converting ethers XX or XXI into a formula IV or VI derivative in which B represents a halogen such as chlorine or bromine, by treatment of ether with acetyl chloride in the presence of tin tetrachloride or with acetyl bromide in the presence of tin tetrabromide, under similar conditions to those described hereinbefore in Section 2.2.

The resulting formula IV or VI intermediates are then converted into formula I compound as described hereinbefore in Section 1.6.

This variant is illustrated in diagrams 10a and 10b.

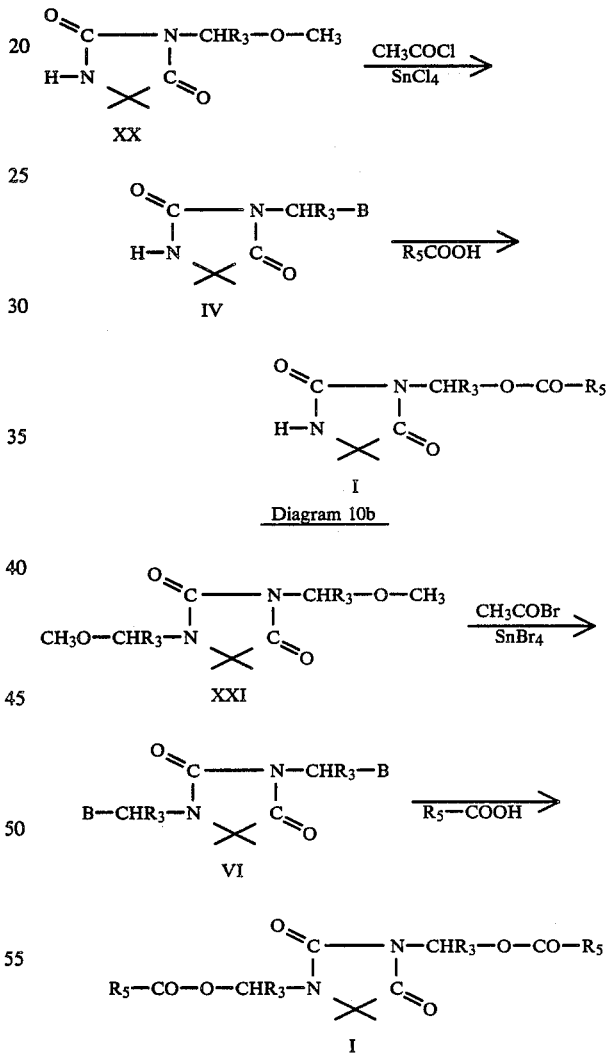

3. In the formula I compounds according to the invention, groups $R_1$ and $R_2$ are not necessarily identical, and formula I compounds in which $R_1$ and $R_2$ are different can easily be prepared by suitably combining the previously-described methods.

By way of non-limitative example, a method of this kind is illustrated in diagram 11 hereinafter.

Diagram 11

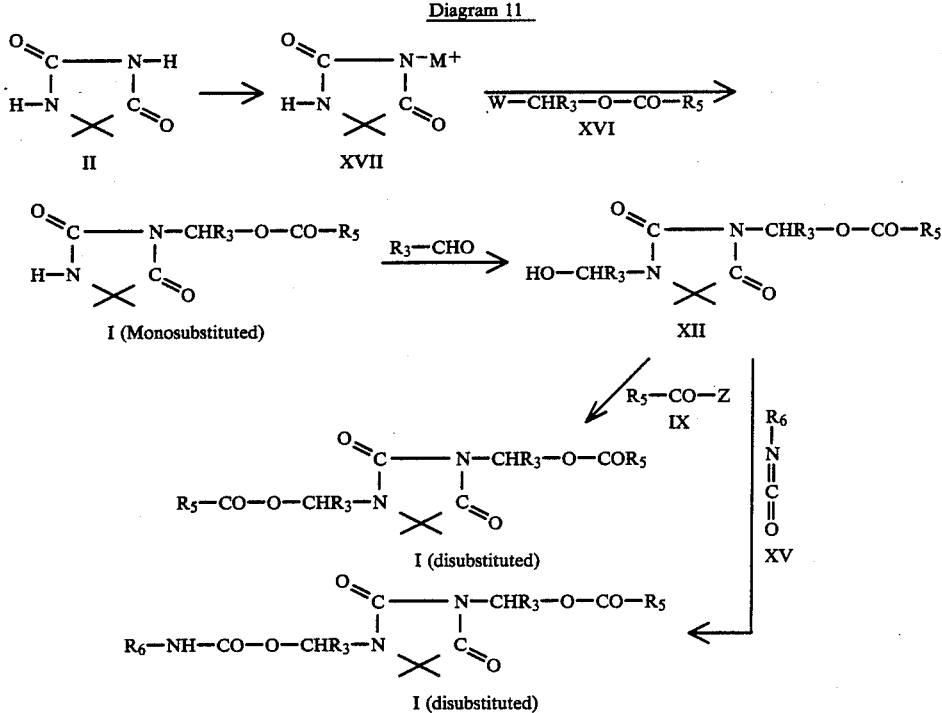

$R_3$, $R_5$, $R_6$, W and $M^+$ have the previously-given meanings except that groups $R_3$ and $R_5$ must not simultaneously have the same values in both substituents of the hydantoin nucleus.

The reaction conditions for these conversions are identical with those previously described for the same kind of reaction, except that care is taken that the reagents and reactions do not affect the other groups already present in the molecule.

4. The starting product for preparing the derivatives according to the invention, i.e. spiro-/fluorene-9,4'-imidazolidine/-2',5'-dione (II) is very easily obtained by a conventional method /W. H. McCown, e.a., J. Am. Chem. Soc., 64, 689 (1942)/ starting from 9-fluorene-one, which is a commercial product, easily obtainable and easy to handle.

Note that the ease with which the products according to the invention can be synthesized distinguishes them from other similar products, e.g. those bearing a substituent on the fluorenyl group.

The following are detailed examples of preparation of some derivatives according to the invention are given by way of non-limitative example thereof.

EXAMPLE A

Synthesis of bis-(1',3'-hydroxymethyl)-spiro-/fluorene-9,4'-imidazolidine/-2',5'-dione. (I: $R_1=R_2=CH_2OH$) (compound No. 1 in Table 1).

Under vigorous agitation, 90 ml of a 37% aqueous solution of formol (1.11M) were added dropwise at ambient temperature to a suspension of 19 g (0.076M) of spiro-/fluorene-9,4'-imidazolidine/-2',5'-dione in 200 ml water containing 1.05 g (0.0076M) of potassium carbonate. The resulting mixture was agitated for 24 hours at ambient temperature; a precipitate formed which was isolated, washed in a 3% aqueous solution of formol and dried. The product was 22 g (95%) of bis-(1',3'-hydroxymethyl)-spiro-/fluorene-9,4'-imidazolidine/-2',5'-dione in the form of a white solid.

M.P.: 165°–170° C. (decomposition).

| Elementary analysis: | C | H | N |
|---|---|---|---|
| % Calculated | 65.83 | 4.55 | 9.03 |
| % found | 65.73 | 4.65 | 9.23 |

EXAMPLE B

Synthesis of bis-(1',3'-acetoxymethyl)-spiro-/fluorene-9,4'-imidazolidine/-2',5'-dione. (I: $R_1=R_2=CH_2-O-CO-CH_3$) (compound No. 2 in Table 1)

1.727 g (0.022M) acetyl chloride was added to a solution of 3.1 g (0.010M) of compound 1 in 15 ml anhydrous pyridine at a speed such that the reaction temperature did not rise above 0° C. The mixture was agitated for a further 24 hours at 0° C. and then poured into 20 ml iced water and the mixture was agitated for a few hours in order to solidify the reaction product. The resulting white powder was isolated, washed in water and dried, yielding 3.3 g (84%) of bis-(1',3'-acetoxymethyl)-spiro-/fluorene-9,4'-imidazolidine/-2',5'-dione.

M.P.: 134° C.

| Elementary analysis: | C | H | N |
|---|---|---|---|
| % calculated | 63.95 | 4.60 | 7.11 |
| % found | 64.01 | 4.61 | 7.37 |

EXAMPLE C

Synthesis of
bis-(1',3'-n.octanoyloxymethyl)-spiro-/fluorene-9,4'-imidazolidine/-2',5'-dione. (I: $R_1=R_2=-CH_2-O-CO-n.C_7H_{15}$) (Compound No. 6 in Table 1)

3.6 g (0.022M) of n.octanoyl chloride were slowly added at 0° C. to a solution of 3.1 g (0.010M) of compound 1 in 15 ml anhydrous pyridine. The reacting substance was agitated at 0° C. for 2 hours, then poured into iced water and extracted with chloroform. The organic solution was washed with 10% hydrochloric acid, dried on MgSO$_4$ and evaporated till dry. The resulting oil (6.5 g) was purified by chromatography on a column (support: SiO$_2$; eluent: chloroform). Fractions were evaporated to dryness to form an oil which solified after a few hours.

The product was 4 g (71%) of bis-(1',3'-n.octanoyloxymethyl)-spiro-/fluorene-9,4'-imidazolidine/-2',5'-dione in the form of wax.

| Elementary analysis: | C | H | N |
|---|---|---|---|
| % calculated | 70.44 | 7.52 | 4.98 |
| % found | 70.32 | 7.48 | 5.48 |

EXAMPLE D

Synthesis of
bis-(1',3'-ethoxycarbonyloxymethyl)-spiro-/fluorene-9,4'-imidazolidine/-2',5'-dione. (I: $R_1=R_2=-CH_2-O-CO-O-C_2H_5$). (Compound No. 10 in Table 1)

1.5 g (0.0141M) of ethyl chloroformate were slowly added at 5° C. to 2 g (0.0064M) of compound No. 1 dissolved in 25 ml anhydrous pyridine. The reaction mixture was kept for a further 2 hours at 0° C. before being poured into iced water. The resulting solid was isolated, dried on P$_2$O$_5$ and recrystallised from methanol, yielding 2.4 g (83%) of bis-(1',3'-ethoxycarbonyloxymethyl)-spiro-/fluorene-9,4'-imidazolidine/-2',5'-dione in the form of a white solid.
M.P.: 132°–133° C.

| Elementary analysis | C | H | N |
|---|---|---|---|
| % calculated | 60.79 | 4.88 | 6.16 |
| % found | 61.05 | 4.99 | 6.06 |

EXAMPLE E

Synthesis of
bis-(1',3'-N-phenylcarbamoyloxymethyl)-spiro-/fluorene-9,4'-imidazolidine/-2',5'-dione. (I: $R_1=R_2=-CH_2-O-CO-NH-C_6H_5$). (Compound No. 18 in Table 1)

In an anhydrous nitrogen atmosphere, 1.7 g (0.0141M) of phenyl isocyanate were slowly added at 5° C. to a solution of 2 g (0.0064M) of product 1 dissolved in 25 ml anhydrous pyridine. The reaction mixture was kept at 0° C. for 2 hours then at ambient temperature for 2 hours and then poured into iced water. The aqueous phase was decanted from the precipitate, which was then agitated in methanol to form a white solid. The product was 3.1 g (88%) of bis-(1',3'-N-phenylcarbamoyloxymethyl)-spiro-/fluorene-9,4'-imidazolidine/-2',5'-dione in hemihydrate form.
M.P.: 218° C. (decomposition).
Water content (Karl Fisher method): % calculated (for hemihydrate): 1.6; % found: 1.5.

| Elementary analysis (hemihydrate): | C | H | N |
|---|---|---|---|
| % calculated | 66.78 | 4.52 | 10.05 |
| % found | 66.75 | 4.48 | 9.99 |

EXAMPLE F

Synthesis of
1'-(methoxymethyl)-spiro-/fluorene-9,4'-imidazolidine/-2',5'-dione. (I: $R_1=-CH_2-O-CH_3$; $R_2=H$. (Compound No. 17 in Table I)

f.1. Synthesis of the sodium mono-salt of spiro-/fluorene-9,4'-imidazolidine/-2',5'-dione. (I: $R_1=Na$; $R_2=H$)

Under anhydrous conditions and in an inert atmosphere, 10 g (0.040M) of spiro-/fluorene-9,4'-imidazolidine/-2',5'-dione (compound II) were added to a methanolic solution of sodium methanolate prepared by dissolving 950 mg (0.041M) sodium in 200 ml anhydrous methanol. The mixture was agitated for 30 minutes at ambient temperature and the solvent was evaporated in vacuo, thus obtaining the sodium mono-salt of compound II in the form of a white powder.

f.2. Synthesis of 1'-(methoxymethyl)-spiro-/fluorene-9,4'-imidazolidine/-2',5'-dione 1.75 g (0.022M) of chloromethyl methyl ether were slowly added to 5 g (0.02M) of the sodium mono-salt of compound II dissolved in 10 ml anhydrous dimethylformamide. The mixture was agitated at ambient temperature for 6 hours, then poured into 100 ml water. The precipitate was isolated and purified by chromatography on a column (support: SiO$_2$; eluent, methanol/chloroform 1/20). The product after solidification from suitable fractions were 1'-(methoxymethyl)-spiro-/fluorene-9,4'-imidazolidine/-2',5'-dione, obtained with a yield of about 80%, in the form of a white solid.
M.P.: 169° C.

| Elementary analysis: | C | H | N |
|---|---|---|---|
| % calculated | 69.37 | 4.79 | 9.52 |
| % found | 69.78 | 4.86 | 9.77 |

EXAMPLE G

Synthesis of
1'-(acetoxymethyl)-spiro-/fluorene-9,4'-imidazolidine/-2',5'-dione. (I: $R_1=-CH_2-O-CO-CH_3$; $R_2=H$). (Compound No. 21 in Table I)

Under anhydrous conditions and in an inert atmosphere, 2.5 g (0.085M) of compound No. 17 (obtained in Example f.2.) were added to 10 ml acetic anhydride containing 100 μl of tin tetrachloride. The mixture was agitated at ambient temperature for 24 hours, then poured into 200 ml water. The precipitate was isolated and agitated hot in a mixture of 20 ml chloroform and 1 ml methanol, then filtered and dried, yielding 1.5 g (55%) of 1'-(acetoxymethyl)-spiro-/fluorene-9,4'- imidazolidine/-2',5'-dione in the form of a white solid. M.P.: 226°–227° C.

| Elementary analysis: | C | H | N |
|---|---|---|---|
| % calculated | 67.07 | 4.38 | 8.69 |
| % found | 66.62 | 4.34 | 8.75 |

EXAMPLE H

Synthesis of 1'-/1-(2,2-dimethylpropanoyloxy)-ethyl/-spiro-/fluorene-9,4'-imidazolidine/-2',5'-dione. (I: $R_1 = -CH(CH_3) - O - CO - t.C_4H_9$; $R_2 = H$). (Compound No. 7 in Table I)

1.1 g (0.0066M) of 2,2-dimethyl 1-chloroethyl propanoate was added to 1.67 g (0.006M) of the sodium mono-salt of compound II (cf. Example f.1.) dissolved in 10 ml anhydrous dimethyl formamide. The reaction medium was first agitated for a few hours at ambient temperature, then 2 hours at 90° C. and then poured into 150 ml iced water. The precipitate was isolated and purified by chromatography on a column (support: SiO$_2$; eluent, methanol/chloroform 5/95). Solidification from suitable fractions yielded 1'-/1-(2,2-dimethylpropanoyloxy)ethyl/-spiro-/fluorene-9,4'-imidazolidine/-2',5'-dione in the form of a white solid. M.P.: 193° C.

| Elementary analysis: | C | H | N |
|---|---|---|---|
| % calculated | 69.82 | 5.86 | 7.40 |
| % found | 69.78 | 5.90 | 7.30 |

Table I hereinafter shows the derivatives prepared in the preceding examples, together with other derivatives according to the invention prepared by the aforementioned methods.

The structures proposed for all these examples have been confirmed by mass spectrometry, infrared spectroscopy, proton nuclear magnetic resonance and elementary analysis (C, H, N).

TABLE I

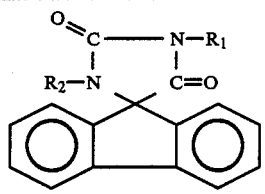

| Compound No. | Code CP-AR | $R_1$ | $R_2$ | M.P. (° C.) | Crystallization solvent |
|---|---|---|---|---|---|
| 1 | 3182 | CH$_2$OH | CH$_2$OH | 165–170[a] | H$_2$O |
| 2 | 3192 | CH$_2$—O—CO—CH$_3$ | CH$_2$—O—CO—CH$_3$ | 134 | H$_2$O |
| 3 | 3193 | CH$_2$—O—CO—C$_6$H$_5$ | CH$_2$—O—CO—C$_6$H$_5$ | 169–170 | H$_2$O |
| 4 | 3212 | CH$_2$—O—CO—t.C$_4$H$_9$ | CH$_2$—O—CO—t.C$_4$H$_9$ | 133 | Et$_2$O—hexane |
| 5 | 3253 | CH$_2$—O—CO—C$_2$H$_5$ | CH$_2$—O—CO—C$_2$H$_5$ | 114–115 | CHCl$_3$—hexane |
| 6 | 3341 | CH$_2$—O—CO—n.C$_7$H$_{15}$ | CH$_2$—O—CO—n.C$_7$H$_{15}$ | cire | [b] |
| 7 | 3373 | CH(CH$_3$)—O—CO—t.C$_4$H$_9$ | H | 193 | CH$_3$OH |
| 8 | 3378 | CH$_2$—O—CO—(CH$_2$)$_3$—C$_6$H$_{11}$ | CH$_2$—O—CO—(CH$_2$)$_3$—C$_6$H$_{11}$ | 67–68 | CH$_3$OH |
| 9 | 3379 | CH$_2$—O—CO—CH$_2$—C(CH$_3$)$_3$ | CH$_2$—O—CO—CH$_2$—C(CH$_3$)$_3$ | 109 | CH$_3$OH |
| 10 | 3387 | CH$_2$—O—CO—O—C$_2$H$_5$ | CH$_2$—O—CO—O—C$_2$H$_5$ | 132–133 | CH$_3$OH |
| 11 | 3409 | CH$_2$—O—CO—(CH$_2$)$_3$—C$_6$H$_5$ | CH$_2$—O—CO—(CH$_2$)$_3$—C$_6$H$_5$ | cire | [b] |
| 12 | 3410 | CH$_2$—O—CO—C$_6$H$_{11}$ | CH$_2$—O—CO—C$_6$H$_{11}$ | 124–125 | CH$_3$OH |
| 13 | 3420 | CH$_2$—O—CO—O—CH$_2$—C$_6$H$_5$ | CH$_2$—O—CO—O—CH$_2$—C$_6$H$_5$ | 52–53 | [b] |
| 14 | 3421 | CH$_2$—O—CO—CH$_2$—O—C$_6$H$_5$ | CH$_2$—O—CO—CH$_2$—O—C$_6$H$_5$ | 52 | Et$_2$O |
| 15 | 3422 | CH$_2$—O—CO—n.C$_4$H$_9$ | CH$_2$—O—CO—n.C$_4$H$_9$ | huile | [b] |
| 16 | 3423 | CH$_2$—O—CO—O—C$_6$H$_5$ | CH$_2$—O—CO—O—C$_6$H$_5$ | 158–159 | H$_2$O |
| 17 | 3425 | CH$_2$—O—CH$_3$ | H | 169 | [b] |
| 18 | 3426 | CH$_2$—O—CO—NH—C$_6$H$_5$ | CH$_2$—O—CO—NH—C$_6$H$_5$ | 218[a,c] | CH$_3$OH |

TABLE I-continued

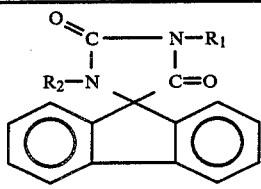

| Compound No. | Code CP-AR | R₁ | R₂ | M.P. (° C.) | Crystallization solvent |
|---|---|---|---|---|---|
| 19 | 3437 | $CH_2-O-CO-\langle H \rangle$ | $CH_2-O-CO-\langle H \rangle$ | 91-92 | $H_2O$ |
| 20 | 3438 | $CH_2-O-CO-\underset{C_2H_5}{CH}-C_6H_5$ | $CH_2-O-CO-\underset{C_2H_5}{CH}-C_6H_5$ | 49-50 | $H_2O$ |
| 21 | 3445 | $CH_2-O-CO-CH_3$ | H | 226-227 | $CH_3OH-CHCl_3$ |
| 22 | 3447 | $CH_2-O-CO-NH-CH_3$ | $CH_2-O-CO-NH-CH_3$ | 168-169 | $CH_3OH-H_2O$ |
| 23 | 3448 | $CH_2-O-CO-CH_2-C_6H_5$ | $CH_2-O-CO-CH_2-C_6H_5$ | 48-50 | $CH_3COOC_2H_5$ |

[a] with decomposition.
[b] purified by chromatography on a column (support: $SiO_2$; eluent: $CHCl_3$)
[c] hemihydrate.

The products according to the invention were given a set of pharmacological and biological tests, the methods and results of which are described hereinafter.

a. Toxicity and Effect on Behaviour

The LD 50 was calculated by the method of Litchfield and Wilcoxon (J. Pharmacol. Exp. Ther., 96, 99, 1949) and is expressed in mg/kg. The products were orally administered to mice.

The effect on behaviour was studied by a method derived from that of S. Irwin (Gordon Res. Conf. on Medicinal Chem., 133, 1959). The substances, suspended in 1% tragacanth mucilage, were orally administered via an intra-gastric probe to groups of 5 male mice fasted for 18 hours. The maximum tested dose was 3 000 mg/kg or 1 000 mg/kg, and smaller doses were tested if an effect has been observed.

Behaviour was studied, 2, 4, 6 and 24 hours after treatment. Observation was continued if symptoms persisted at that time. Deaths were recorded during the 14 days after treatment. The results are given in Table II, in which the numbers of the compounds are the same as the numbers given in column 1 of Table I.

B. Evaluation of Inhibiting Effect on Aldose Reductase

The inhibiting effect of the products according to the invention on aldose reductase was tested in vitro and in vivo.

1. Evaluation in vitro 1.1 Inhibiting effect on enzymatic activity of aldose reductase:

The method described by S. Hayman and J. H. Kinoshita (J. Biol. Chem., 240, 877 (1965)) was used for in vitro testing of the aforementioned effect of the products according to the invention.

Rat's crystalline lens was homogenized in water and centrifuged to eliminate insoluble substances. The supernatant liquid formed the enzyme solution used for the test.

The effect of products according to the invention in inhibiting enzymatic activity of aldose reductase was determined by spectrophotometrically following for 5 minutes the disappearance of NADPH in an aqueous solution containing 0.067M phosphate buffer (final pH: 6.2), 0.40M lithium sulphate, $5.10^{-5}M$ NADPH, $10^{-4}M$ of the product under test and 100 μl of the enzyme solution, to which $10^{-2}M$ of D,L-glyceraldehyde had been added as substrate. (NADPH=reduced form of nicotinamide adenine dinucleotide phosphate).

The inhibiting effect observed in the presence of $10^{-4}M$ of product under test relative to the reaction in the absence of a compound according to the invention, is expressed as a percentage.

The results are given in Table II.

1.2 Inhibiting effect on accumulation of galactitol:

A test for evaluating this activity was made in vitro on fibroblasts obtained from human skin.

An experimental model culture was obtained by incubating the cells in the presence of a medium containing a high concentration of galactose (3 mg/ml) and the product under test, and measuring the accumulation of galactitol in the cells after a 48-hour incubation period at 37° C. The cells were then isolated, washed in physiological salt solution and treated with a water-ethanol solution. The medium was centrifuged and the supernatant liquid was lyophilized.

The galactitol in the resulting sample was determined by HPLC (=high pressure liquid chromatography) after derivatives had been obtained with phenyl isocyanate.

The proportion of proteins in the precipitate obtained during the previously-mentioned centrifuging was measured by the method of M. M. Bradford (Anal. Biochem., 72, 248-254 (1976)) and indicated the number of cells present in the sample.

The inhibiting effect of the tested product was expressed as a percentage inhibition of intracellular accumulation of galactitol compared with the controls.

Product No. 1 (CP 3182 AR) and No. 5 (CP 3253 AR) were tested at doses varying from $10^{-4}$ to $10^{-6}M$. The result show powerful inhibition of the enzymatic activity of aldose reductase in converting galactose to galactitol. At doses of $10^{-4}M$, $10^{-5}M$ and $10^{-6}M$ the inhibition of accumulation of galactitol by compound No. 1 is 85%, 58% and 21% respectively, the corresponding figures for compound No. 5 being 91%, 56% and 24%.

2. Evaluation in vivo 2.1 Inhibition of accumulation of sorbitol in crystalline lenses and nerves of diabetic rats:

The effects of the products according to the invention on the proportion of plasma glucose and the accumulation of sorbitol in the crystalline lenses and sciatic nerves of rats made diabetic by streptozotocin were examined by the method of M. J. Peterson, et al (Metabolism, 28, 456–461 (1979)).

Fasted Sprague Dawley rats were made diabetic by intraperitoneal injection of streptozotocin (75 mg/kg). The product under test was orally administered at a dose of 25 mg/kg after 0, 7 and 24 hours. The rats were sacrificed 27 hours after induction of diabetes. The crystalline lenses and sciatic nerves were taken and preserved at −20° C. until analysed. The crystalline lenses and sciatic nerves were homogenized in water and the proteins were precipitated from ethanol. The precipitate was eliminated by centrifuging and the supernatant liquid was lyophylised. The sorbitol in the sample was determined by the method of B. Bjorkqvist (J. of Chromatograph, 218, 65–71 (1981)), adapted by A. Lenaers et al. (Arch. Intern. Physiol. Bioch., 91, B, 62–63 (1983)).

The sample was dissolved in pyridine containing galactitol as an internal standard. Derivatives were formed therefrom by phenylisocyanate during incubation for 1 hour at 60° C. The reaction was then stopped by adding methanol and the derivatives were separated and determined by HPLC.

The results are expressed as percentage inhibition of the accumulation of sorbitol, compared with the controls. The results are given in Table II.

The proportion of plasma glucose was determined in blood taken at the moment when the rat was sacrificed, using a "Kit Boehringer No. 608.459 ®" (registered mark of Boehringer & Sohn, G.m.b.H.).

No effect of the products according to the invention was observed on the proportion of plasma glucose in rats made diabetic.

The results in Table II show that the products according to the invention markedly inhibit accumulation of sorbitol in the crystalline lenses and sciatic nerves of rats made diabetic. Products Nos. 1, 2, 5, 8, 10, 17, 19 and 21 were found particularly active in this respect.

Under the experimental conditions, sorbinil inhibits accumulation of sorbitol by 93% and 85% respectively in the crystalline lenses and sciatic nerves of rats made diabetic.

TABLE II

| | | | Biological Results | | |
|---|---|---|---|---|---|
| | | | | Inhibition of accumulation of sorbitol in vivo | |
| CP No. | CP-AR Code | Lethal dose LD50 (mg/kg) | Inhibition of enzymatic activity of AR in vitro % | crystalline lenses (%) | in sciatic nerves (%) |
| 1 | 3182 | >3000 | 34 | 81 | 85 |
| 2 | 3192 | >3000 | insol.* | 86 | 85 |
| 3 | 3193 | >3000 | insol. | 37 | 55 |
| 4 | 3212 | | insol. | 51 | 50 |
| 5 | 3253 | | insol. | 74 | 81 |
| 6 | 3341 | >3000 | 0 | 76 | 79 |
| 7 | 3373 | | insol. | 45 | 72 |
| 8 | 3378 | >3000 | insol. | 69 | 85 |
| 9 | 3379 | >1000 | insol. | 49 | 70 |
| 10 | 3387 | >3000 | insol. | 80 | 84 |
| 11 | 3409 | | 0 | 4 | 24 |
| 12 | 3410 | >1000 | insol. | 12 | 48 |
| 13 | 3420 | | insol. | 33 | 50 |
| 14 | 3421 | >1000 | insol. | 51 | 61 |
| 15 | 3422 | | 0 | 54 | 74 |
| 16 | 3423 | >3000 | insol. | 53 | 65 |
| 17 | 3425 | | 84 | 86 | 92 |
| 18 | 3426 | >3000 | insol. | 8 | 17 |
| 19 | 3437 | >3000 | insol. | 77 | 89 |
| 20 | 3438 | >3000 | insol. | 60 | 77 |
| 21 | 3445 | >1000 | 8 | 85 | 94 |
| 22 | 3447 | | 0 | 21 | 17 |
| 23 | 3448 | | insol | 5 | 7 |

*Insol.:Product insoluble in the tested medium and $10^{-4}$ M.

The products according to the invention showed very little toxicity. The lethal dose (LD50) was higher than 3 g/kg for most of the products tested. Furthermore, no tested product induced abnormal behaviour in the mouse. The products therefore are considerably less toxic than other related products such as sorbinil. Sorbinil has an LD50 of 1450 mg/kg and, at a dose of 3 000 mg/kg, all the mice died on the second day. It also induces considerable side-effects at a dose of 300 mg/kg, inter alia depression with loss of righting reflex and muscular hypotonia. These side effects are long-lasting, for more than 24 hours.

It was also shown that compound No. 2 (CP 3192 AR) does not have a mutagenic effect in the Ames test or teratogenic effect on mice at oral doses of 100 mg/kg and 1 000 mg/kg.

2.2 Effect of "in vivo" doses on sorbitol accumulation in sciatic nerves and crystalline lenses of diabetic rats:

Compound No. 1 (CP 3182 AR) and No. 2 (CP 3192 AR) were evaluated at various doses, using the experimental model described hereinbefore (§2.1).

In the case of each product, 25 Sprague Dawley rats fasted the previous day were made diabetic by an intraperitoneal injection of streptozotocin (75 mg/kg). The rats were divided into 5 groups of 5, each orally given 0.3, 1.3 or 10 mg/kg of CP 3182 AR or a control.

An identical experiment was performed with CP 3192 AR at the same doses. Treatment was given immediately after the streptozotocin, and 7 and 24 hours later. The animals were sacrificed 27 hours after induction. Estimates were made of the effects of the products on the proportion of plasma glucose and the sorbitol content of the crystalline lenses and sciatic nerves of rats.

The results of these experiments are given in Table III. They show that the inhibiting effect on sorbitol accumulation are dose-dependent and are already significant at doses as low as 0.3 mg/kg per os.

TABLE III

Effects of doses of compounds 1 and 2 in the diabetic rat model

| | Compound No. 1 (CP 3182 AR) | | | Compound No. 2 (CP 3192 AR) | | |
|---|---|---|---|---|---|---|
| | Plasma | % inhibition of sorbitol accumulation | | Plasma | % inhibition of sorbitol accumulation | |
| Dose (mg/kg) | glucose* (mg/100 ml) | Crystalline lenses | Sciatic nerves | glucose* (mg/100 ml) | Crystalline lenses | Sciatic nerves |
| 0.3 | 462 ± 60 | 0 ± 21 | 29 ± 14 | 425 ± 82 | 3 ± 25 | 42 ± 9 |
| 1 | 538 ± 34 | 1 ± 3 | 41 ± 10 | 444 ± 76 | 13 ± 20 | 40 ± 17 |
| 3 | 464 ± 62 | 41 ± 7 | 69 ± 8 | 446 ± 70 | 46 ± 10 | 68 ± 11 |
| 10 | 424 ± 37 | 71 ± 7 | 82 ± 6 | 472 ± 55 | 66 ± 7 | 79 ± 9 |
| 0 | 404 ± 55 | 0 ± 16 | 0 ± 8 | 404 ± 55 | 0 ± 16 | 0 ± 8 |

*n = 5: Average value ± standard deviation

The therapeutic value of the products according to the invention is also shown by the therapeutic index MED/ED50 (i.e. the ratio of the minimum dose at which a side effect is observed (MED) to the dose at which the measured inhibition of aldose reductase activity is 50% (ED50)).

This index was about 1 000 in the case of crystalline lenses and above 3 000 in the case of sciatic nerves for compounds 1 and 2. The index for sorbinil, on the other hand, is only 300, in the case both of crystalline lenses and sciatic nerves.

The respective MED values are >3 000 mg/kg for compounds 1 and 2 (no side effect was observed at a dose of 3000 mg/kg) and 300 mg/kg for sorbinil. The ED50 values of compounds 1 and 2 were 3 mg/kg for crystalline lenses and 1 mg/kg for sciatic nerves, whereas the ED50 for sorbinil was 1 mg/kg in both cases (cf. 2.2). This therapeutic index clearly shows that the therapeutic value of compounds 1 and 2 is 3.3 to 10 times as high as that of sorbinil.

2.3. In vivo effects of a single dose of compound No. 2 (CP 3192 AR) on the variation in the proportion of plasma glucose and the accumulation of sorbitol in the crystalline lenses and sciatic nerves of diabetic rats.

2.3.1. Preventive effect. CP 3192 AR was administered simultaneously with the induction of diabetes. The experiment was performed on 33 male Sprague Dawley rats weighing about 200 g.

At time 0 hours, 3 rats were sacrificed and used as non-diabetic controls. 30 fats fasted the previous day were made diabetic by an intraperitoneal injection of streptozotocin (75 mg/kg). A dose of 10 mg/kg of CP 3192 AR was simultaneously administered orally to 15 of the rats. The other 15 were given a placebo. 3 control rats and 3 rats treated with CP 3192 AR were sacrificed 2, 4, 8, 24 and 48 hours after induction of diabetes.

An estimate was made of the effects of the product on the proportion of plasma glucose and the sorbitol content of the crystalline lenses and sciatic nerves.

The test results are given in Table IV. They show that the kinetics of accumulation of glucose in the plasma are quite different from that for sorbitol in the crystalline lenses and sciatic nerves of rats made diabetic.

Compound No. 2 (CP 3192 AR) has no effect on the proportion of plasma glucose. On the other hand the effects of a single dose of 10 mg/kg of CP 3192 AR were observed as soon as soribol began to accumulate, both in the crystalline lenses and the sciatic nerves of diabetic rats, and continued at least 48 hours after administration of the product.

TABLE IV

Preventive effect of a single oral dose of 10 mg/kg of compound No. 2 (CP 3192 AR) in rats made diabetic (n = 3; averages ± standard deviation)

| | Plasmaglucose (mg/100 ml) | | Accumulation of sorbitol | | | |
|---|---|---|---|---|---|---|
| Sacrifice | | | in crystalline lenses (μg) | | in sciatic nerves (μg) | |
| (t: hours) | Controls | Treated | Controls | Treated | Controls | Treated |
| 0 | 85.5 ± 0.7 | | 2.67 ± 0.58 | | 1.07 ± 0.15 | |
| 2 | 417 ± 36 | 436 ± 45 | 3 ± 0 | 3 ± 0 | 3.6 ± 1.4 | 1.23 ± 0.2* |
| 4 | 394 ± 14 | 359 ± 45 | 9 ± 1 | 6.3 ± 0.6** | 3.4 ± 0.3 | 1.8 ± 0.2** |
| 8 | 313 ± 9 | 264 ± 73 | 24 ± 7 | 12.3 ± 4.0* | 4.0 ± 0.4 | 1.8 ± 0.5*** |
| 24 | 482 ± 31 | 485 ± 35 | 82.7 ± 14.3 | 52 ± 10.1* | 6.0 ± 0.7 | 4.0 ± 1.0* |
| 48 | 464 ± 31 | 447 ± 34 | 132.3 ± 43.5 | 92.7 ± 18.6 | 8.3 ± 0.6 | 4.6 ± 1.7* |

*$p < 0.05$;
**$p < 0.005$;
***$p < 0.0005$ (Student t test).

2.3.2. Curative effect: CP 3192 AR was administered 24 hours after induction of diabetes.

As before, the experiment was made on 33 male Sprague Dawley rats weighing about 200 g. The 33 rats, which had been fasted the previous day, were made diabetic by an intraperitoneal injection of streptozotocin (75 mg/kg).

24 hours after induction of diabetes, 3 rats were sacrificed and used as diabetic controls. A dose of 10 mg/kg of CP 3192 AR was orally administered to 15 rats whereas the other 15 were given the excipient without an active product. 3 control rats and 3 rats treated with CP 3192 AR were sacrificed 2, 4, 8, 24 and 48 hours after administration of the product.

Estimates were made of the effects of the product on the proportion of plasma glucose and the sorbitol content of the crystalline lenses and sciatic nerves of rats made diabetic by streptozotocin.

The test results are given in Table V.

They show that, as in the preceding experiment, CP 3192 AR at the dose used had no effect on the proportion of plasma glucose. On the other hand a single dose of 10 mg/kg of CP 3192 AR completely inhibits the accumulation of sorbitol in the crystalline lenses of diabetic rats and greatly reduces the proportion of sorbitol in the sciatic nerves thereof. As in the preceding test, the effects of the product continued for 48 hours or even longer.

TABLE V

Curative effect of a single oral dose of 10 mg/kg of Compound No. 2 (CP 3192 AR) administered 24 hours after induction of diabetes in rats. (n = 3; averages ± standard deviation).

| Sacrifice $(t = h)^x$ | Plasma glucose (mg/100 ml) | | Accumulation of sorbitol | | | |
|---|---|---|---|---|---|---|
| | | | in crystalline lenses (µg) | | in sciatic nerves (µg) | |
| | Control | Treated | Control | Treated | Control | Treated |
| 0 | 483 ± 36 | | 122 ± 35 | | 8.0 ± 2.2 | |
| 2 | 454 ± 21 | 406 ± 28 | 122 ± 28 | 103 ± 27 | $7.0^a$ | 4.8 ± 2.0 |
| 4 | 409 ± 32 | 459 ± 73 | 130 ± 30 | 99 ± 5 | — | $4.0^a$ |
| 8 | 466 ± 38 | 575 ± 14 | 132 ± 12 | 125 ± 8 | 7.3 ± 0.7 | $2.2^a$ |
| 24 | 465 ± 10 | 478 ± 83 | 202 ± 33 | 73 ± 18*** | $8.9^a$ | 2.5 ± 0.4 |
| 48 | 476 ± 99 | 456 ± 117 | 360 ± 115 | 142 ± 47* | 7.3 ± 2.5 | 5.9 ± 1.8 |

$^x$time in hours after administration of compound No. 2
*p < 0.05,
**p < 0.005;
***p <0.0005 (Student t test).
$^a$n = 1.

The previously-described biological results clearly show the potential importance of products according to the invention in the prevention and treatment of complications of diabetes such as cataracts, neuropathy, retinopathy, nephropathy, vasculopathy and galactosemia.

The compounds according to the invention are administered to man orally at daily doses from 20 mg to 5,000 mg or parenterally at daily doses of 10 to 2,000 mg or locally at daily doses of 1 to 250 mg.

The products according to the invention can be administered in various galenic forms.

By way of non-limitative example, the following are some examples of galenic formulations in which the active principle is a compound according to the invention, denoted by the letter A.

The active principle can be chosen from among the compounds Numbered 1, 2, 5, 6, 7, 8, 10, 17, 18 and 21 in Table I.

| Tablet | |
|---|---|
| A | 100 mg |
| Corn starch | 50 mg |
| Polyvinyl pyrrolidone | 10 mg |
| Micro-crystalline cellulose | 100 mg |
| Talc | 10 mg |
| Ac-Di-Sol ® | 5 mg |
| Magnesium stearate | 1 mg |
| Tablet | |
| A | 250 mg |
| Micro-crystalline cellulose | 75 mg |
| Hydroxypropylmethyl cellulose | 10 mg |
| Micro-crystalline cellulose | 75 mg |
| Starch 1500 ® | 100 mg |
| Explotab ® | 10 mg |
| Magnesium stearate | 1 mg |
| Injectable I.M. | |
| A | 25 mg |
| Ethylenediamine tetraacetate | 5 mg |
| Benzyl alcohol | 5 mg |
| Purified water ad | 1 ml |
| Eye lotion | |
| A | 10 mg |
| Ethylenediamine tetraacetate | 5 mg |
| Methyl p-hydroxybenzoate | 1.5 mg |
| Propyl p-hydroxybenzoate | 0.5 mg |
| Purified water ad | 1 ml |

Ac-Di-Sol ®: registered mark for cross-linked carboxymethylcellulose
Starch 1500 ®: registered mark for pregelatinised starch
Explotab ®: registered mark for sodium salt of carboxymethyl starch.

What is claimed is:

1. A compound of the formula

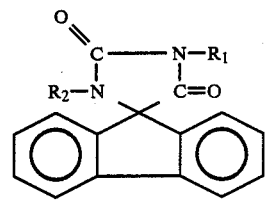

in which:
R1 and R2, which may or may not be identical, represent:
(a) Hydrogen or
(b) A CHR3—OR4 group in which R3 represents:
(1) Hydrogen
(2) A straight-chain or branched C1, C2, C3 or C4 alkyl group or
(3) A phenyl group,
R4 represents:
(1) Hydrogen
(2) A straight-chain or branched C1, C2, C3, C4, C5, C6, C7, C8, C9 or C10 alkyl group,
(3) A C3, C4, C5, C6, C7 or C8 cycloalkyl group
(4) A straight-chain or branched C1, C2, C3 or C4 alkyl group substituted by:
(a) A phenyl or phenoxy group, or
(b) A phenyl or phenoxy group substituted by one or more C1, C2, C3, or C4 alkyl or C1, C2, C3 or C4 alkoxy radicals or by one or two atoms of fluorine, chlorine or bromine,
(5) A phenyl group, unsubstituted or substituted by one or two C1, C2, C3, C4 alkyl or C1, C2, C3, C4 alkoxy radicals or by one or two atoms of fluorine, chlorine or bromine
(6) A

group in which $R_5$ represents:

(a) A straight-chain or branched $C_1$, $C_2$, $C_3$, $C_4$, $C_5$, $C_6$, $C_7$, $C_8$, $C_9$ or $C_{10}$ alkyl group (b) A $C_5$, $C_6$ or $C_7$ cycloalkyl group (c) A straight-chain or branched $C_1$, $C_2$, $C_3$, $C_4$ or $C_5$ alkyl group substituted by a radical chosen from among the following group:
A $C_5$, $C_6$, $C_7$ cycloalkyl radical,
A phenyl or phenoxy radical,
A phenyl or phenoxy radical substituted by one, two or three straight-chain or branched $C_1$, $C_2$, $C_3$, $C_4$ alkyl or $C_1$, $C_2$, $C_3$, $C_4$ alkoxy groups or by one or two atoms of fluorine, chlorine or bromine, (d) A phenyl group (e) An —NH—$R_6$ group in which $R_6$ represents hydrogen or a straight-chain or branched $C_1$, $C_2$, $C_3$, $C_4$ alkyl group or a phenyl group (f) An —OR—$R_7$ group in which $R_7$ represents a straight-chain or branched $C_1$, $C_2$, $C_3$, $C_4$ alkyl group or a phenyl or benzyl group, with the restriction that $R_1$ and $R_2$ are not simultaneously hydrogen, or a stereoisomer or a mixture of stereoisomers or a salt of said compound formed with a pharmaceutically useful metal or organic base.

2. A compound according to claim 1, characterised in that in formula I, $R_1$ and $R_2$ represent a group $CHR_3$—$OR_4$ in which $R_3$ represents hydrogen or a $C_1$-$C_4$ alkyl group and $R_4$ represents a group —CO—$R_5$ in which $R_5$ represents a straight-chain or branched $C_1$-$C_{10}$ alkyl group or a straight-chain or branched $C_5$-$C_7$ cycloalkyl or $C_1$-$C_5$alkyl group substituted by a $C_5$-$C_7$ cycloalkyl.

3. A compound according to claim 1, characterised in that in formula I, $R_1$ and $R_2$, which may or may not be identical, represent hydrogen or a group $CHR_3$—O—CO—$R_5$ in which $R_3$ represents hydrogen or a methyl group and $R_5$ represents a straight-chain or branched $C_1$-$C_{10}$ alkyl group with the restriction that $R_1$ and $R_2$ do not simultaneously represent hydrogen.

4. A compound according to claim 1, characterised in that in formula I, $R_1$ and $R_2$ represent a group —CH$R_3OR_4$ in which $R_4$ represents a group CO—$OR_7$ in which $R_7$ represents a $C_1$-$C_4$ alkyl group or a phenyl or benzyl group.

5. A compound according to claim 1, characterised in that in formula I, $R_1$ and $R_2$, in which may or may not be identical, represent hydrogen or a group $CHR_3$—$OR_4$ in which $R_3$ represents a hydrogen group or a $C_1$-$C_3$ alkyl group and $R_4$ represents hydrogen or a straight-chain or branched $C_1$-$C_5$ alkyl group, with the restriction that $R_1$ and $R_2$ do not simultaneously represent hydrogen.

6. A compound according to claim 1, characterised in that in formula I, $R_1$ and $R_2$, which may be identical or not, represent hydrogen or a group $CHR_3$—$OR_4$ in which $R_4$ represents a phenyl group which may be substituted by one or two methyl or methoxy radicals or by one or two atoms of fluorine, chlorine or bromine with the restriction that $R_1$ and $R_2$ do not simultaneously represent hydrogen.

7. A compound according to claim 1, characterised in that in formula I, $R_1$ and $R_2$, which may be identical or not, represent hydrogen or a $CHR_3$—$OR_4$ group in which $R_3$ represents hydrogen or a $C_1$-$C_4$ alkyl group and $R_4$ represents a straight-chain or branched $C_1$-$C_{10}$ alkyl group or a $C_3$-$C_8$ cycloalkyl group or a $C_1$-$C_4$ alkyl group substituted by a phenyl or phenoxy group which may be substituted, with the restriction that $R_1$ and $R_2$ do not simultaneously represent hydrogen.

8. A compound according to claim 1, characterised in that in formula I, $R_1$ and $R_2$ represent a group $CHR_3$—$OR_4$ in which $R_3$ represents hydrogen or a $C_1$-$C_4$ alkyl group and $R_4$ represents a group CO—N-H—$R_6$ in which $R_6$ represents oxygen or a $C_1$-$C_4$ alkyl group or a phenyl group.

9. A compound according to claim 1, characterised in that formula I, $R_1$ and $R_2$ represent the group $CHR_3$—$OR_4$ in which $R_3$ represents hydrogen or a $C_1$-$C_4$ alkyl group and $R_4$ represents a group CO—$R_5$ in which $R_5$ represents a phenyl group or a straight-chain or branched $C_1$-$C_5$ alkyl group substituted by a phenyl or phenoxy group substituted if required by a methyl or methoxy radial or by an atom of fluorine, chlorine or bromine.

10. A compound according to claim 1, characterised in that in formula I, $R_1$ and $R_2$, which may or may not be identical, represent hydrogen or a group $CHR_3$—$OR_4$ in which $R_3$ represents a phenyl group, with the restriction that $R_1$ and $R_2$ may not simultaneously be hydrogen.

11. A compound according to claim 1, characterised in that $R_1$ and $R_2$ are identical but different from hydrogen.

12. A compound according to claim 1, characterised in that $R_2$ represents hydrogen.

13. A compound according to claim 1, characterised in that $R_3$ represents hydrogen.

14. A compound according to claim 1, characterised in that it is chosen from among the group formed by the following compounds:
bis-(1',3'-hydroxymethyl)-spiro-[fluorene-9,4'-imidazolidine]-2',5'-dione
bis-(1',3'-acetoxymethyl)-spiro-[fluorene-9,4'-imidazolidine]-2',5'-dione
bis-(1',3'-n.octanoyloxymethyl-spiro-[fluorene-9,4'-imidazolidine]-2',5'-dione
bis-(1',3'-ethoxycarbonyloxymethyl)-spiro-[fluorene-9,4'-imidazolidine]-2',5'-dione
1'-methoxymethyl-spiro-[fluorene-9,4'-imidazolidine]-2',5'-dione
1'-acetoxymethyl-spiro-[fluorene-9,4'-imidazolidine]-2',5'-dione
bis-(1',3'-N-phenylcarbamoyloxymethyl)-spiro-[fluorene-9,4'-imidazolidine]-2',5'-dione
bis-[1',3'-(4-cyclohexylbutanoyloxymethyl)]-spiro-[fluorene-9,4'-imidazolidine]-2',5'-dione
1'-[1-(2,2-dimethylpropanoyloxy)ethyl]-spiro-[fluorene-9,4'-imidazolidine]-2',5'-dione
bis-(1',3'-propanoyloxymethyl)-spiro-[fluorene-9,4'-imidazolidine]-2',5'-dione.

15. A pharmaceutical composition characterised in that it comprises a therapeutically effective amount of at least one compound of formula I or salt thereof associated with a suitable pharmaceutical excipient:

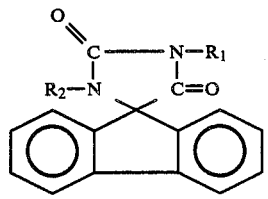

in which:

$R_1$ and $R_2$, which may or may not be identical, represent:
(a) Hydrogen or
(b) A $CHR_3$—$OR_4$ group in which $R_3$ represents:
  (1) Hydrogen
  (2) A straight-chain or branched $C_1$, $C_2$, $C_3$ or $C_4$ alkyl group or
  (3) A phenyl group,
$R_4$ represents:
  (1) Hydrogen
  (2) A straight-chain or branched $C_1$, $C_2$, $C_3$, $C_4$, $C_5$, $C_6$, $C_7$, $C_8$, $C_9$ or $C_{10}$ alkyl group,
  (3) A $C_3$, $C_4$, $C_5$, $C_6$, $C_7$ or $C_8$ cycloalkyl group
  (4) A straight-chain or branched $C_1$, $C_2$, $C_3$ or $C_4$ alkyl group substituted by:
    (a) A phenyl or phenoxy group, or
    (b) A phenyl or phenoxy group substituted by one or more $C_1$, $C_2$, $C_3$, or $C_4$ alkyl or $C_1$, $C_2$, $C_3$ or $C_4$ alkoxy radicals or by one or two atoms of fluorine, chlorine or bromine,
  (5) A phenyl group, substituted if required by one or two $C_1$, $C_2$, $C_3$, or $C_4$ alkyl or $C_1$, $C_2$, $C_3$, $C_4$ alkoxy radicals or by one or two atoms of fluorine, chlorine or bromine
  (6) A

group in which $R_5$ represents:
  (a) A straight-chain or branched $C_1$, $C_2$, $C_3$, $C_4$, $C_5$, $C_6$, $C_7$, $C_8$, $C_9$ or $C_{10}$ alkyl group
  (b) A $C_5$, $C_6$ or $C_7$ cycloalkyl group
  (c) A straight-chain or branched $C_1$, $C_2$, $C_3$, $C_4$ or $C_5$ alkyl group substituted by a radical chosen from among the following group:
    A $C_5$, $C_6$, $C_7$ cycloalkyl radical,
    A phenyl or phenoxy radical,
    A phenyl or phenoxy radical substituted by one, two or three straight-chain or branched $C_1$, $C_2$, $C_3$, $C_4$ alkyl or $C_1$, $C_2$, $C_3$, $C_4$ alkoxy groups or by one or two atoms of fluorine, chlorine or bromine,
  (d) A phenyl group
  (e) An —NH—$R_6$ group in which $R_6$ represents hydrogen or a straight-chain or branched $C_1$, $C_2$, $C_3$, $C_4$ alkyl group or a phenyl group
  (f) An —O—$R_7$ group in which $R_7$ represents a straight-chain or branched $C_1$, $C_2$, $C_3$, $C_4$ alkyl group or a phenyl or benzyl group, with the restriction that $R_1$ and $R_2$ are not simultaneously hydrogen, or a stereoisomer or a mixture of stereoisomers or a salt of said compound formed with a pharmaceutically useful metal or organic base.

16. A pharmaceutical composition according to claim 15 in the form of dragées, granules, tablets, capsules, solutions, syrups, emulsions or suspensions.

17. A method of inhibiting aldose reductase activity which comprises administering to a mammal in need thereof a therapeutically effective amount of a compound of the formula (I):

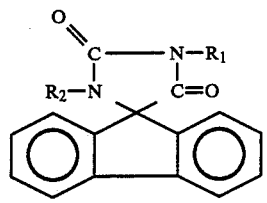 (I)

in which:
$R_1$ and $R_2$, which may or may not be identical, represent:
(a) Hydrogen or
(b) A $CHR_3$—$OR_4$ group in which $R_3$ represents:
  (1) Hydrogen
  (2) A straight-chain or branched $C_1$, $C_2$, $C_3$ or $C_4$ alkyl group or
  (3) A phenyl group,
$R_4$ represents:
  (1) Hydrogen
  (2) A straight-chain or branched $C_1$, $C_2$, $C_3$, $C_4$, $C_5$, $C_6$, $C_7$, $C_8$, $C_9$ or $C_{10}$ alkyl group,
  (3) A $C_3$, $C_4$, $C_5$, $C_6$, $C_7$ or $C_8$ cycloalkyl group
  (4) A straight-chain or branched $C_1$, $C_2$, $C_3$ or $C_4$ alkyl group substituted by:
    (a) A phenyl or phenoxy group, or
    (b) A phenyl or phenoxy group substituted by one or more $C_1$, $C_2$, $C_3$, or $C_4$ alkyl or $C_1$, $C_2$, $C_3$ or $C_4$ alkoxy radicals or by one or two atoms of fluorine, chlorine or bromine,
  (5) A phenyl group, substituted if required by one or two $C_1$, $C_2$, $C_3$, $C_4$ alkyl or $C_1$, $C_2$, $C_3$, $C_4$ alkoxy radicals or by one or two atoms of fluorine, chlorine or bromine
  (6) A

group in which $R_5$ represents:
  (a) A straight-chain or branched $C_1$, $C_2$, $C_3$, $C_4$, $C_5$, $C_6$, $C_7$, $C_8$, $C_9$ or $C_{10}$ alkyl group
  (b) A $C_5$, $C_6$ or $C_7$ cycloalkyl group
  (c) A straight-chain or branched $C_1$, $C_2$, $C_3$, $C_4$ or $C_5$ alkyl group substituted by a radical chosen from among the following group:
    A $C_5$, $C_6$, $C_7$ cycloalkyl radical,
    A phenyl or phenoxy radical,
    A phenyl or phenoxy radical substituted by one, two or three straight-chain or branched $C_1$, $C_2$, $C_3$, $C_4$ alkyl or $C_1$, $C_2$, $C_3$, $C_4$ alkoxy groups or by one or two atoms of fluorine, chlorine or bromine,
  (d) A phenyl group
  (e) An —NH—$R_6$ group in which $R_6$ represents hydrogen or a straight-chain or branched $C_1$, $C_2$, $C_3$, $C_4$ alkyl group or a phenyl group
  (f) An —O—$R_7$ group in which $R_7$ represents a straight-chain or branched $C_1$, $C_2$, $C_3$, $C_4$ alkyl group or a phenyl or benzyl group, with the restriction that $R_1$ and $R_2$ are not simultaneously hydrogen, or a stereoisomer or a mixture of stereoisomers or a salt of said compound formed with a pharmaceutically useful metal or organic base.

18. A method of preventing or treating I neuropathy, cataract, retinopathy, nephropathy or vasculopathy associated with diabetic conditions, or complications of galactosemia which comprises administering to a mammal in need thereof a therapeutically effective amount of a compound of the formula (I)

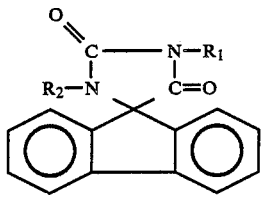

in which:

$R_1$ and $R_2$, which may or may not be identical, represent:

(a) Hydrogen or (b) A $CHR_2$—$OR_4$ group in which $R_3$ represents:
  (1) Hydrogen
  (2) A straight-chain or branched $C_1$, $C_2$, $C_3$ or $C_4$ alkyl group or
  (3) A phenyl group, $R_4$ represents:
  (1) Hydrogen
  (2) A straight-chain or branched $C_1$, $C_2$, $C_3$, $C_4$, $C_5$, $C_6$, $C_7$, $C_8$, $C_9$ or $C_{10}$ alkyl group,
  (3) A $C_3$, $C_4$, $C_5$, $C_6$, $C_7$ or $C_8$ cycloalkyl group
  (4) A straight-chain or branched $C_1$, $C_2$, $C_3$ or $C_4$ alkyl group substituted by:
    (a) A phenyl or phenoxy group, or
    (b) A phenyl or phenoxy group substituted by one or more $C_1$, $C_2$, $C_3$, or $C_4$ alkyl or $C_1$, $C_2$, $C_3$ or $C_4$ alkoxy radicals or by one or two atoms of fluorine, chlorine or bromine,
  (5) A phenyl group, substituted if required by one or two $C_1$, $C_2$, $C_3$, $C_4$ alkyl or $C_1$, $C_2$, $C_3$, $C_4$ alkoxy radicals or by one or two atoms of fluorine, chlorine or bromine
  (6) A

group in which $R_5$ represents:
  (a) A straight-chain or branched $C_1$, $C_2$, $C_3$, $C_4$, $C_5$, $C_6$, $C_7$, $C_8$, $C_9$ or $C_{10}$ alkyl group
  (b) A $C_5$, $C_6$ or $C_7$ cycloalkyl group
  (c) A straight-chain or branched $C_1$, $C_2$, $C_3$, $C_4$ or $C_5$ alkyl group substituted by a radical chosen from among the following group:
    A $C_5$, $C_6$, $C_7$ cycloalkyl radical,
    A phenyl or phenoxy radical,
    A phenyl or phenoxy radical substituted by one, two or three straight-chain or branched $C_1$, $C_2$, $C_3$, $C_4$ alkyl or $C_1$, $C_2$, $C_3$, $C_4$ alkoxy groups or by one or two atoms or fluorine, chlorine or bromine,
  (d) A phenyl group
  (e) An —NH—$R_6$ group in which $R_6$ represents hydrogen or a straight-chain or branched $C_1$, $C_2$, $C_3$, $C_4$ alkyl group or a phenyl group
  (f) An —OR—$R_7$ group in which $R_7$ represents a straight-chain or branched $C_1$, $C_2$, $C_3$, $C_4$ alkyl group or a phenyl or benzyl group, with the restriction that $R_1$ and $R_2$ are not simultaneously hydrogen, or a stereoisomer or a mixture of stereoisomers or a salf of said compound formed with a pharmaceutically useful metal or organic base.

* * * * *